(12) United States Patent
Leahy (10) Patent No.: US 8,579,989 B2
(45) Date of Patent: Nov. 12, 2013

(54) DEVICE AND METHOD FOR USE IN PARIETAL SURGERY

(76) Inventor: Patrick Leahy, Dublin (IE)

( * ) Notice: Subject to any disclaimer, the term of this patent is extended or adjusted under 35 U.S.C. 154(b) by 716 days.

(21) Appl. No.: 10/553,929

(22) PCT Filed: Apr. 22, 2004

(86) PCT No.: PCT/EP2004/004380
§ 371 (c)(1),
(2), (4) Date: Aug. 29, 2006

(87) PCT Pub. No.: WO2004/093690
PCT Pub. Date: Nov. 4, 2004

(65) Prior Publication Data
US 2007/0066980 A1 Mar. 22, 2007

(30) Foreign Application Priority Data
Apr. 22, 2003 (IE) .................. S2003/0303

(51) Int. Cl.
*A61F 2/02* (2006.01)
(52) U.S. Cl.
USPC ....................................... 623/23.72
(58) Field of Classification Search
USPC .................... 600/201, 204, 209; 604/29, 502;
623/23.64, 23.72, 23.65; 606/151, 191,
606/192, 193, 194, 195, 198, 199, 200
See application file for complete search history.

(56) References Cited

U.S. PATENT DOCUMENTS

| | | | |
|---|---|---|---|
| 4,762,128 A | 8/1988 | Rosenbluth | |
| 5,176,692 A | 1/1993 | Wilk et al. | |
| 5,275,610 A * | 1/1994 | Eberbach | 606/198 |
| 5,333,624 A | 8/1994 | Tovey | |
| 5,405,360 A | 4/1995 | Tovey | |
| 5,522,790 A * | 6/1996 | Moll et al. | 600/204 |
| 5,853,411 A * | 12/1998 | Whayne et al. | 606/41 |
| 6,368,338 B1 * | 4/2002 | Konya et al. | 606/200 |
| 6,375,668 B1 * | 4/2002 | Gifford et al. | 606/200 |
| 6,605,037 B1 * | 8/2003 | Moll et al. | 600/204 |

(Continued)

FOREIGN PATENT DOCUMENTS

| | | |
|---|---|---|
| EP | 1275351 | 1/2003 |
| WO | WO 9530374 | 11/1995 |

OTHER PUBLICATIONS

An Office Action Rejection for European publication EP1617766, which is the foreign counterpart to the present application.

(Continued)

*Primary Examiner* — Thomas McEvoy
(74) *Attorney, Agent, or Firm* — Gardner, Linn, Burkhart & Flory, LLP (57) ABSTRACT

The present invention provides a device (10; 110) for use in parietal surgery, in particular for use in laparascopic hernia repair, the device (10; 110) comprising a body (12; 138) at one end of which is located a parietal reinforcement implant (14; 114), in a collapsed state, the device (10; 110) including means operate e to expose the parietal surgical implant from within the body, and means operable to urge the parietal surgical implant (14; 114) into an open or expanded state, once positioned at the site of the hernia, wherein the parietal surgical implant (14; 114) may be separated from the device (10; 110), in order to allow the parietal surgical implant (14; 114) to be secured against the site of the hernia such as to aid in the healing of same.

22 Claims, 5 Drawing Sheets

(56) References Cited

U.S. PATENT DOCUMENTS

| | | | |
|---|---|---|---|
| 6,958,074 B2 * | 10/2005 | Russell | 606/200 |
| 7,048,752 B2 * | 5/2006 | Mazzocchi et al. | 606/200 |
| 2002/0143349 A1 * | 10/2002 | Gifford et al. | 606/157 |
| 2003/0004579 A1 * | 1/2003 | Rousseau et al. | 623/23.72 |
| 2003/0073979 A1 | 4/2003 | Naimark et al. | |
| 2003/0171739 A1 * | 9/2003 | Murphy et al. | 606/1 |

OTHER PUBLICATIONS

The rejected claims from European publication EP1617766, which is the foreign counterpart to the present application.

* cited by examiner

DEVICE AND METHOD FOR USE IN PARIETAL SURGERY

The present invention is concerned with a device for use in parietal surgery, and in particular a device for use in parietal surgery for hernia repair, more particularly laparoscopic hernia repair. The surgical device of the present invention may also be used to repair incision sites following surgery.

The occurrence of a hernia, whether abdominal or hiatal, is one of the most common ailments, and estimates suggest that approximately 5 million Americans have an abdominal hernia of one form or another. An abdominal hernia occurs when tissue or an organ protrudes through a weak or ruptured section of the muscles or tissue lining the abdominal cavity. Such a weakened or ruptured section may be congenital, or may occur as a result of an injury or prior surgical procedure.

Although only a small percentage of people with a hernia seek treatment, hernia repair is still one of the most frequently performed operations, with approximately half a million annually in the United States. The traditional method for repairing a hernia involves the creation of an incision in the wall of the patient's abdomen, adjacent the site of the hernia itself, and forcing the protruding tissue/intestine back into position within the abdominal cavity. Occasionally, the hernia may be non reducible, meaning that the protruding tissue cannot be forced back into the abdominal cavity, and must be surgically removed. This will normally be the case where "strangulation" has occurred, namely that the rupture through which the tissue protrudes is so tight that the blood supply to the protruding tissue has been cut off, resulting in death of the tissue. Once the tissue has been replaced or removed, the abdominal wall is then surgically closed, securing the tissue/intestine in place.

Over the past two decades, this technique has been greatly assisted by the inclusion of a parietal surgical implant in the form of a mesh or support, usually of synthetic material, which, following the removal of the tissue from, or replacement of the tissue into, the abdominal cavity, is seated against the site of the ruptured parietal, for example abdominal, lining, in order to reinforce the rupture and prevent the reopening of same. The incision in the abdomen is then surgically closed over the mesh, which is thus held secure against the ruptured lining, greatly increasing the effectiveness of the procedure.

In more recent years, laparoscopic surgery has been used when performing hernia repair, due to the advantages thereof. This type of surgery requires less recovery time, and leaves very little scarring, due to the reduced size of the incision necessary to perform the surgery. Laparoscopic surgery does however employ different techniques to conventional surgery, and could be said to be more awkward than normal surgery, due to a lack of direct "hands on" contact by the surgeon. For this reason alone, many surgeons are unwilling or unable to perform this type of surgery, despite the benefits which may be achieved.

The present invention therefore seeks to overcome the problems associated with parietal surgery, in particular by providing a device for use in parietal surgery, in particular for use when performing hernia repair surgery.

The present invention therefore provides, in a first aspect, a device for use in parietal surgery, the device comprising a body; a parietal surgical implant, the parietal surgical implant being locatable in a collapsed state about or within the body, the parietal surgical implant being adapted to be displaceable between the collapsed state and an expanded state; and means for expanding the parietal surgical implant from the collapsed state into the expanded state.

Preferably, the parietal surgical implant is locatable within the body; and means are provided for retaining the parietal surgical implant within the body in the collapsed state, the retaining means being operable to expose the parietal surgical implant. Alternatively, the body comprises a shaft and the parietal surgical implant is locatable in the collapsed state about the shaft.

Preferably, the retaining means comprises a sleeve within which the parietal surgical implant is locatable, the sleeve being displaceable relative to the parietal surgical implant in order to expose the parietal surgical implant.

Preferably, the body is of elongate tubular form.

Preferably, the device further comprises an actuator operable to effect displacement of the sleeve relative to the parietal surgical implant.

Preferably, the body is provided with means for gripping the body in order to facilitate manipulation of the device.

Preferably, the actuator is located at or adjacent the gripping means, the actuator being operatively associated with the sleeve.

Preferably, the actuator is mounted for slidable engagement with the body.

Preferably, the parietal surgical implant comprises a mesh having a mesh perimeter and a shaft mounting area, the mesh being mounted to a shaft; and the expanding means is slidably mounted about the shaft, the expanding means being displaceable towards the mesh, in order to urge the mesh towards the expanded state.

Preferably, the expanding means comprises a collar slidably mounted about the shaft, and at least one arm mounted between the collar and an arm mounting position of the mesh, the arm mounting position being spaced apart from the shaft mounting area.

Preferably, the expanding means comprises a plurality of arms mounted about the collar, the plurality of arms being secured to a plurality of the arm mounting positions of the mesh, the arm mounting positions being spaced apart from the shaft mounting area.

Preferably, the or each arm mounting position is located adjacent the mesh perimeter. More preferably, the plurality of arm mounting position are spaced apart on the mesh perimeter.

Preferably, the shaft mounting area is substantially centrally located.

Preferably, the mesh is substantially circular and the shaft mounting area is located substantially centrally therein; and the plurality of arm mounting positions are circumferentially spaced apart on the mesh perimeter.

Preferably, the shaft is provided with a shaft handle displaceable relative to the body, such that the mesh may be drawn towards the expanding means in order to effect expansion of the mesh.

Preferably, the mesh is separable from the shaft.

Preferably, the mesh and the shaft are adapted for a press fit engagement.

Alternatively, the shaft is formed from a material which may be cut by conventional surgical equipment.

Preferably, the device further comprises an abutment against which, in use, the mesh may be seated, once separated from the shaft, in order to secure the mesh in place.

Preferably, the parietal surgical implant is formed from a biodegradable material.

Preferably, the body is provided with a distensible member thereon.

Preferably, the distensible member comprises a balloon connectable to a fluid supply in order to effect the inflation thereof.

According to a second aspect of the invention, there is provided a parietal surgical implant for use as a replacement part for a device according to the first aspect of the invention, the parietal surgical implant being provided in a collapsed state, and being adapted to be displaceable between the collapsed state and an expanded state.

Preferably, the parietal surgical implant comprises a mesh having a mesh perimeter and a shaft mounting area, the mesh being mounted to a shaft; and expanding means slidably mounted about the shaft, the expanding means being displaceable towards the mesh in order to urge the mesh towards the expanded state.

Preferably, the expanding means comprises a collar slidably mounted about the shaft, and at least one arm mounted between the collar and an arm mounting position of the mesh, the arm mounting position being spaced apart from the shaft mounting area.

Preferably, the expanding means comprises a plurality of arms mounted about the collar, the plurality of arms being secured to a plurality of the arm mounting positions of the mesh, the arm mounting positions being spaced apart from the shaft mounting area.

According to a third aspect of the present invention, there is provided a method of surgical repair at a surgical repair site, comprising the steps of:
providing a device according to the first aspect of the invention;
passing the parietal surgical implant, in the collapsed state, through an incision into a position adjacent the surgical repair site;
expanding the parietal surgical implant from the collapsed state into an expanded state; and
securing the parietal surgical implant against the surgical site.

Optionally, the method further comprises the steps of:
providing the parietal surgical implant as a mesh mounted in a collapsed state about or within the body;
providing expanding means slidably mounted on the body; and
expanding the mesh by displacing the expanding means towards the mesh, in order to urge the mesh towards the expanded state.

As used herein, the term "parietal surgery" is intended to mean surgery to repair or reinforce any wall defining a hollow cavity in a human or animal. This includes, but is not limited to, hernias such as inguinal and incisional hernias.

As used herein, the term "body" is intended to mean any component, or collection of components, which forms the backbone or main element of a device, and may be formed from any suitable material or composite of materials which embody the requisite structural and/or functional characteristics for the intended application. In it's simplest embodiment, the term "body" comprises a shaft.

As used herein, the term "parietal surgical implant" is intended to mean any element, whether laminar or otherwise, flexible or solid, permeable or impermeable, which may be employed as an abutment for location/fixation against a site of weakened or ruptured tissue or the like, in order to reinforce the site during the healing of same, thus improving and accelerating the healing process. Preferably, the parietal surgical implant has a parietal face which is located, in use, against the abdominal or thoracic wall and an opposing visceral face. The parietal face of the implant is preferably adapted to encourage soft tissue ingrowth therein and the visceral face is preferably adapted to inhibit tissue attachment thereto.

As used herein, the term "actuator" is intended to mean any device or mechanism, whether operated mechanically, electrically, hydraulically, pneumatically, or a combination thereof, or by any other means, which is capable of effecting the relative displacement, in particular the remote relative displacement, of the sleeve relative to the parietal surgical implant.

As used herein, the term "mesh" is intended to mean a flexible, laminar or sheet like element or otherwise, which is preferably reticulated or perforated, and which may be formed from any suitable material, preferably a bio-compatible, and optionally biodegradable, polymer or the like.

As used herein, the term "distensible" is intended to mean the ability to distend or expand/deform/displace outwardly in order to be capable of enlarging a space, in particular for the purposes of aiding a laparascopic surgical procedure, and may be achieved by inflation, mechanical displacement, or by any other suitable means.

The present invention will now be described with reference to the accompanying drawings, in which.

Figure 5:
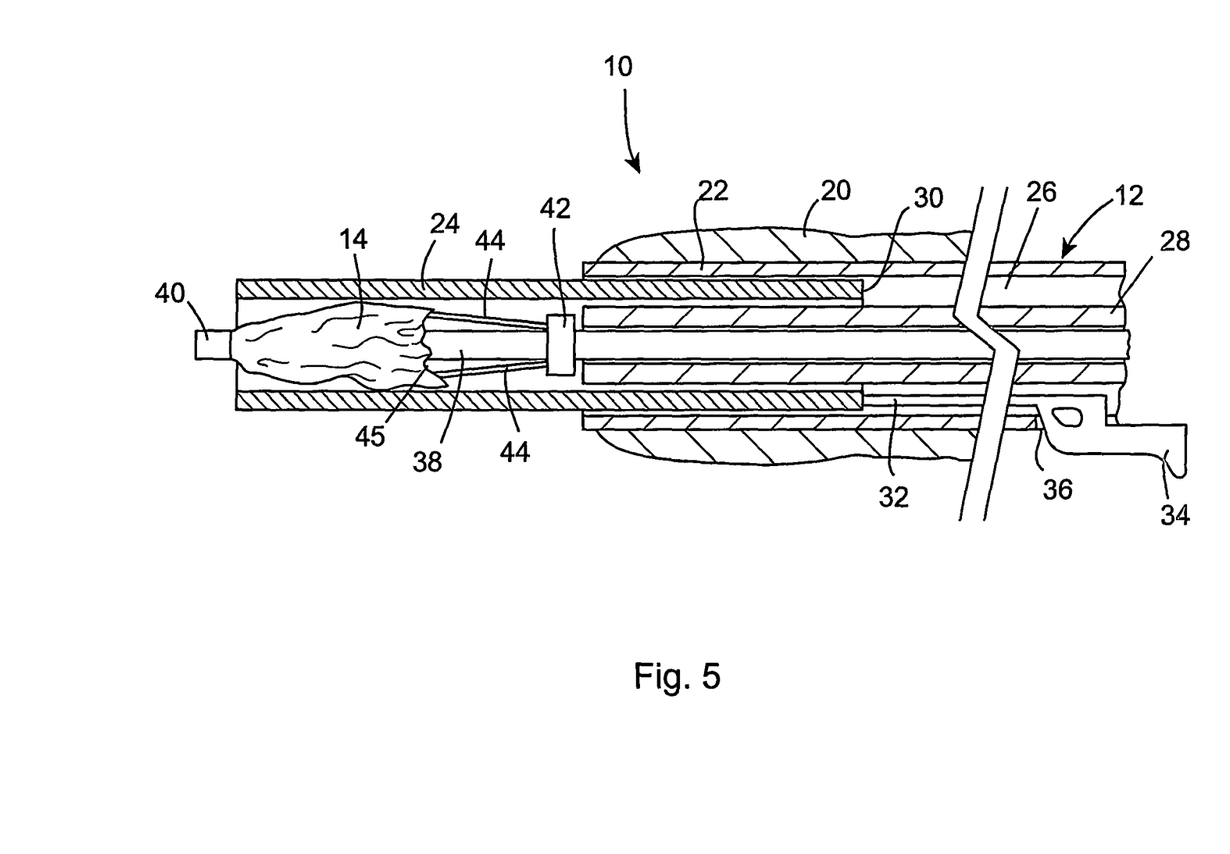
FIG. 5 illustrates a sectioned side elevation of the device of FIG. 1 for use in parietal surgery, illustrating the internal configuration thereof in the undeployed configuration of FIG. 1.

Referring now to FIGS. 1 to 5 of the accompanying drawings, there is illustrated an embodiment of a device for use in parietal surgery, generally indicated as 10, for particular use in hernia repair surgery, and more particularly for laparoscopic hernia repair. Abdominal hernias may be inguinal, epigastric, umbilical, phemerol or incisional, all of which are repaired in the same basic manner and, as described above, all of which are suitable to be repaired with the aid of the device 10 of the present invention. The device 10 comprises a body 12 in which may be stored a parietal surgical implant in the form of a mesh 14, as can be seen in FIG. 5. As will be explained in detail hereinafter, the device 10 is configured to be inserted through a conventional abdominal incision at or adjacent the site of a hernia (not shown), and to deploy the mesh 14 against the ruptured abdominal wall. The mesh 14 is then secured in place by closure of the surgical incision, the mesh 14 thereby being retained in situ in order to reinforce the rupture site, and therefore aid in healing of the hernia, in conventional fashion. The mesh 14 is of a type currently used in hernia repair surgery, with slight modifications, as will be described hereinafter, in order to render the mesh 14 suitable for deployment by the device 10.

Figure 1:
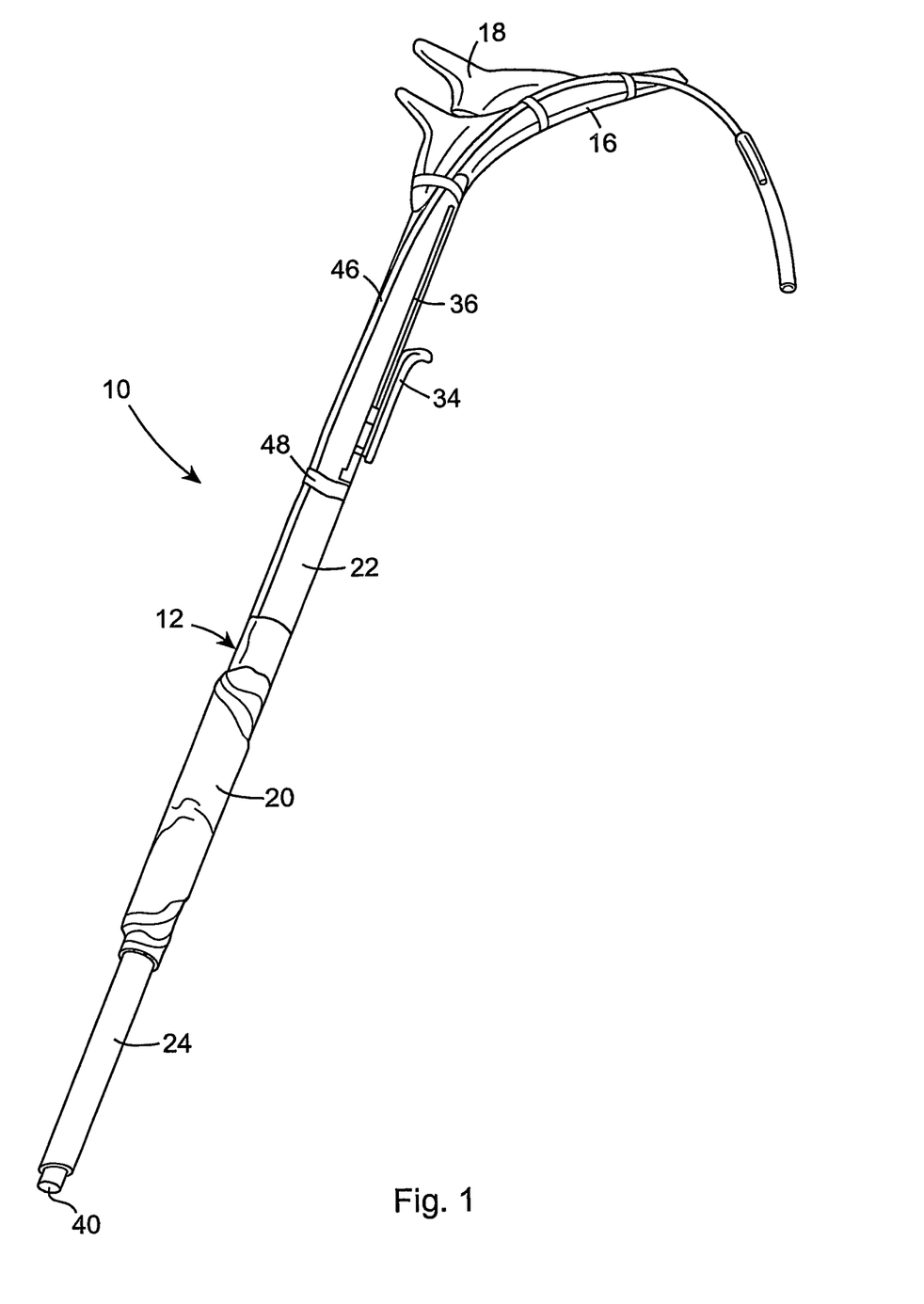
FIG. 1 illustrates a perspective view of a device for use in parietal surgery according to a preferred embodiment of the invention, in an undeployed configuration.
Figure 2:
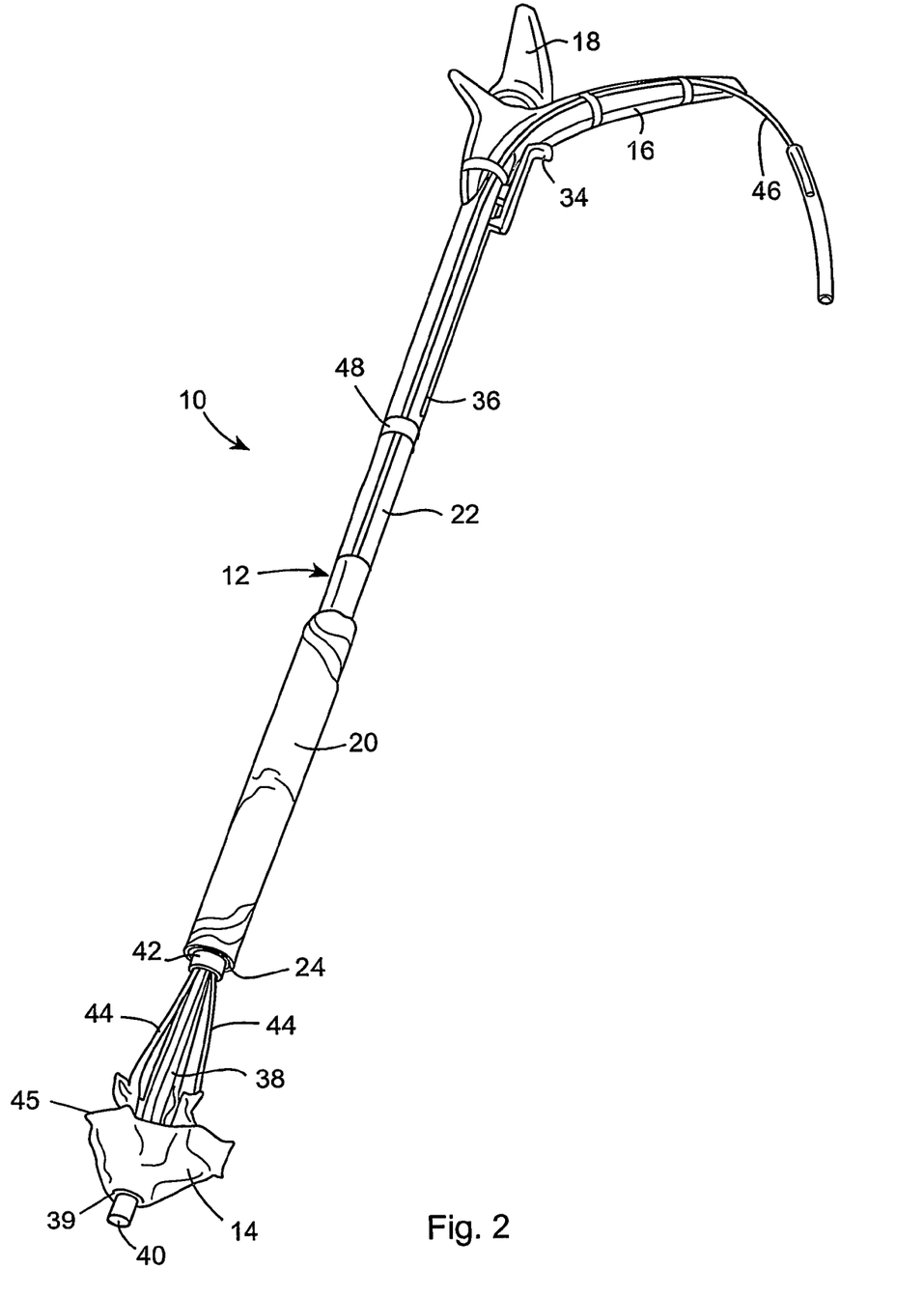
FIG. 2 illustrates a perspective view of the device for use in parietal surgery of FIG. 1, in a partially deployed configuration in which a sleeve has been retracted in order to expose a mesh which is otherwise contained or housed within the device.

As the device 10 is intended for use in laparoscopic or "keyhole" surgery, the body 12 is elongate in form, having a small cross-sectional area in order to allow the body 12 to pass through a small incision (not shown) in the abdominal wall or the like. Ideally, the body 12 is a hollow cylinder. The length of the body 12 may be varied in order to suit the type/location of the hernia to be operated on, thereby varying the depth, within the surgical cavity, to which the device 10 is capable of reaching or extending. The exterior surface of the body 12, or more particularly the finish thereof, is preferably smooth and uninterrupted, in order to facilitate the smooth insertion and removal of the body 12 into and out of the surgical cavity. The body 12 is preferably curvilinear, more preferably, circular in transverse cross-section.

The device 10 includes gripping means in the form of a first handle 16 and a shaft handle in the form of a second handle 18 at one end of the device 10, (the end distal the mesh 14) in order to facilitate manipulation of the device 10 during use, as will be described hereinafter in detail. The first handle 16 extends from the body 12 and is shaped and dimensioned to permit a surgeon to hold the device 10 in place, and to manipulate same. Alternatively, the body 12 of the device 10 may be modified to permit the surgeon to directly grip the body 12 (not shown). Adjacent an opposed end of the device 10 is a distensible member in the form of a balloon 20 which may be inflated during use of the device 10, in order to create a cavity within the abdomen, into which a fibre optic camera (not shown) or the like may be inserted, in order to aid in the surgical procedure. The balloon 20 is not an essential element of the invention, but does improve the functionality of same. For example, separate provisions could be made, during the surgical procedure, to distend the abdominal cavity. The balloon 20 is also preferably provided with a sheath (not shown) adhered around the balloon 20, prior to the inflation of the balloon 20, which sheath serves to maintain the balloon 20 in the collapsed state shown, and which also preserves the elasticity of the balloon 20, by preventing the drying out of the material used to form the balloon 20. The sheath is preferably formed from a cellulose material, which simply splits or ruptures on inflation of the balloon 20, for example as manufactured by Inamed Corporation, Santa Barbara, Calif., the United States.

The body 12 comprises a tubular housing 22, at one end of which is located the first and second handles 16, 18 and at the opposed end of which is located retaining means in the form of a sleeve 24. The sleeve 24 is shaped and dimensioned to receive and retain the mesh 14 in a collapsed state, as can be seen in FIG. 5. The sleeve 24, in the preferred embodiment illustrated, is shaped and dimensioned to be retractable within the housing 22, in order to expose the mesh 14. Therefore, the sleeve 24 will prevent the mesh 14 from being opened or deployed while the sleeve 24 is in the extended state, as shown in FIGS. 1 and 5.

In order to allow retraction of the sleeve 24 into the housing 22, the body 12 is provided with a correspondingly dimensioned annular cavity 26 defined between the housing 22 and an inner tube 28 located concentrically within the housing 22. In order to actually effect retraction of the sleeve 24, which will be disposed within the surgical cavity during use, and therefore not directly accessible, an inner end 30 of the sleeve 24 is connected to an actuator in the form of a rod 32 and a trigger 34 connected to the rod 32, which rod 32/trigger 34 are operable to remotely retract or extend the sleeve 24 as required. The rod 32 extends rearwardly from the sleeve 24, within the cavity 26, with the trigger 34 being located externally of the body 12, adjacent the first and second handles 16, 18. The trigger 34 is slideably mounted within a track or keyway 36 in the housing 22, so that retraction of the trigger 34 along the keyway 36 will effect retraction of the sleeve 24, thus exposing the mesh 14. During use, the portion of the housing 22 containing the keyway 36 will be located externally of the surgical cavity and adjacent the handles 16, 18, and the trigger 34 may therefore be manually operated by the surgeon, without having to relinquish grip of one or both of the handles 16, 18.

The retractable sleeve 24 provides a number of functions, in order to improve the performance of the device 10. The sleeve 24 is primarily intended to provide a covering over the mesh 14 during insertion of the device 10 into the surgical cavity, presenting a smooth surface about the mesh 14, which will therefore prevent the mesh 14 from snagging or tearing the surrounding tissue and prevent damage or contamination of the mesh 14 itself. To a certain extent, the sleeve 24 also maintains the mesh 14 in the collapsed state illustrated in FIG. 5, although as will be described hereinafter, the device 10 does employ additional components to achieve this. In particular, as mentioned hereinbefore, the mesh 14 cannot be deployed while the sleeve 24 is in the extended state illustrated in FIGS. 1 and 5.

It will therefore be appreciated that it is the functionality of the sleeve 24, as opposed to the specific configuration of same, that is important in terms of the retaining means functionality of the device 10. Thus any other suitable arrangement may be employed which is operable to selectively cover and expose the mesh 14. For example, the sleeve 24 could be fixed relative to the body 12, and the mesh 14 actively displaced from within the sleeve 24, thus achieving exposure of the mesh 14. Alternatively, the sleeve 24 could be replaced with some form of dissolvable sheath or wrap (not shown) which, once inserted into the surgical cavity, would dissolve in order to expose the mesh 14, or which sheath may simply be mechanically weak, such that the mesh 14, in being deployed into the expanded state, would rupture the sheath.

It will also be apparent that the trigger 34, and the rod 32 connecting same to the sleeve 24, could be replaced with any other suitable alternative actuator embodying the functionality of same, namely the capacity to retract or extend the sleeve 24, in particular the remote actuation of same. For example, the device 10 could be provided with an electrical power supply (not shown), such as a battery or the like, with the device 10 being modified to function like a solenoid, with the sleeve 24 acting as the core, which would thus retract upon the application of a current to a coil (not shown) suitably located within the device 10, and suitably insulated in order to guard against electric shocks from the device 10. The sleeve 24 could be spring-loaded in order to return to the extended position upon termination of the electrical current. With such an arrangement, a simple depressible button (not shown) or the like could be provided on the first handle 16 in order to effect retraction of the sleeve 24. It will of course be apparent that such a configuration would greatly increase the complexity and cost of the device 10, and that a simple mechanical actuator arrangement, as of the illustrated embodiment, is preferred.

Figures 3, 4:
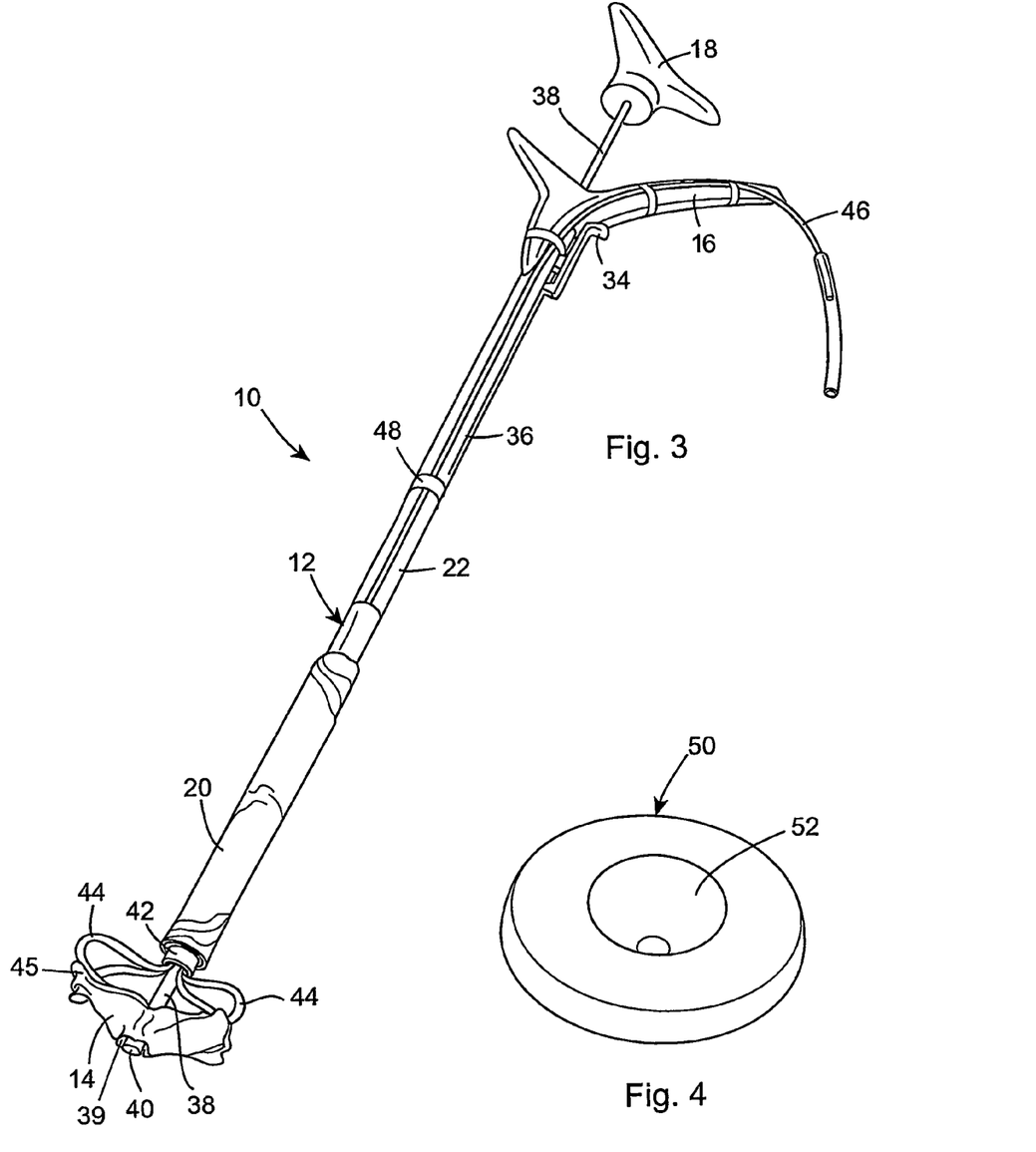
FIG. 3 illustrates a perspective view of the device illustrated in FIG. 1, in which device the mesh has been forced towards an open position in readiness for use.
FIG. 4 illustrates a rear perspective view of an abutment for use with the device of FIG. 1.

Once the mesh 14 has been exposed in the collapsed state, in the present embodiment by retraction of the sleeve 24, the mesh 14 must then be expanded towards an expanded state, before being secured in place against the site of the hernia. The mesh 14 is mounted on a shaft 38 via a shaft mounting area 39, which shaft 38 defines a tip 40. The shaft 38 extends through the body 12, thereby serving to secure the mesh 14 to the body 12. A collar 42 is slidably mounted on the shaft 38, adjacent the mesh 14, from which collar 42 extends a plurality of arms 44, the arms 44 preferably being formed from a flexible material, each arm 44 being secured to the mesh 14 at various points about a mesh perimeter 45 of the mesh 14. If the mesh 14 is disc shaped, then the plurality of arms 44 are secured at locations circumferentially spaced apart on the mesh perimeter 45. The shaft 38 passes through the collar 42, and extends through the body 12, within the inner tube 28, exiting the body 12 adjacent the first handle 16. The shaft 38 terminates in the second handle 18. The collar 42 and arms 44 form expanding means which are operable to urge the mesh 14 towards the expanded state as shown in FIG. 3. Referring in particular to FIG. 5, the collar 42 is shaped and dimensioned for a sliding fit on the shaft 38, and has an outside diameter sufficiently small to be locatable within the sleeve 24, but sufficiently large to be unable to pass through the inner tube 28. Thus, with the sleeve 24 retracted, the second handle 18 may be drawn rearwardly away from the body 12, thereby drawing the shaft mounting area 39 of the mesh 14 towards the inner tube 28. However, as the collar 42 cannot pass through the inner tube 28, drawing the second handle 18 away from the body 12, forces the collar 42 against the inner tube 28 and further drawing of the second handle 18 away from the body 12 causes the mesh 14 to be drawn towards the collar 42. This relative movement causes the flexible arms 44 to act against the mesh 14, thereby forcing the mesh 14 to unfurl into the expanded state shown in FIG. 3. In this condition, the mesh 14 is ready to be separated from the device 10, as will be described hereinafter in detail, and secured in place by closing the surgical incision in the parietal, for example abdominal, wall.

Although in the embodiment illustrated, each arm 44 is secured to the mesh 14 at a point on the mesh perimeter 45, it will be appreciated that in order to perform the necessary function of unfurling the mesh 14, each arm 44 need only be connected to the mesh 14 at a position spaced apart from the shaft mounting area 39. Thus the arms 44 could, for example, be located intermediate, for example half way, between the shaft mounting area 39 and the mesh perimeter 45. However, the greatest leverage for unfurling the mesh 14 will be achieved by positioning the arms 44 at the mesh perimeter 45, as in the illustrated embodiment.

It will also be appreciated that the arms 44 are preferably hingedly mounted to the collar 42, in order to allow the arms 44 to hinge outwardly, in use, away from the shaft 38 in response to displacement of the collar 42 relative to the mesh 14. In the embodiment illustrated, the flexibility of the arms 44 creates a virtual or flexible hinge between each arm 44 and the collar 42. It will of course be understood that the arms 44 could be rigid in form, with a suitable hinge (not shown) being provided between each arm 44 and the collar 42.

From the above description, it will be apparent that it is the relative movement between the collar 42 and the mesh 14 that effects expansion of the mesh 14 into the expanded state. It will thus be apparent that, rather than drawing the shaft 38 rearwardly through the body 12 thereby retracting the shaft 38 into the body 12, the inner tube 28 could be forwardly displaced, by suitable means, towards the mesh 14, with the shaft 38 remaining stationery, thereby extending the inner tube 28 out of the body 12, the same relative movement between the collar 42 and the mesh 14 being achieved. It will also be appreciated that the expanding means for effecting deployment of the mesh 14 is one way of achieving the intended function, and that any other suitable arrangement could be employed. For example, the mesh 14 could be provided with suitable resilience or "memory", such as to immediately deploy itself upon retraction of the sleeve 24 or extension of the inner tube 28. In such a case, the collar 42 and arms 44 could be omitted.

As a further alternative, the mesh 14 could be provided with a network of capillary tubes (not shown) or the like, such that a fluid, preferably a gas such as air, could be pumped into the mesh 14 in order to inflate same, thereby deploying the mesh 14 into the expanded state. To this end, the illustrated embodiment of the device 10 already includes a tube 46 in fluid communication with the balloon 20, in order to enable the balloon 20 to be connected, in use, to a remote fluid reservoir (not shown), such as a gas supply, in order to allow the balloon 20 to be inflated. A further gas supply line or tube (not shown) could therefore be provide in fluid communication with such a modified mesh (not shown), in order to effect the inflation of same and deploy the mesh 14 into the expanded state.

Once the mesh 14 has been deployed, as shown in FIG. 3, the mesh 14 must then be separated from the remainder of the device 10 in order to allow withdrawal of the device 10 from within the surgical cavity, such that the surgical incision providing access to the hernia may be closed and the mesh 14 secured in place, as will be described in detail hereinafter. In the preferred embodiment illustrated, when the mesh 14 is in the expanded state, as shown in FIG. 3, the second handle 18 is spaced rearwardly from the first handle 16, such that a length of the shaft 38 is exposed between the handles 16, 18. In order to facilitate removal of the device 10 from the abdominal cavity, the second handle 18 is separable from the shaft 38, thereby allowing the body 12 to be drawn rearwardly along the shaft 38, until the body 12 has been drawn completely off the shaft 38, at which point the body 12 is redundant, and can be set aside for possible re-use, if desired.

In order to allow the second handle 18 to be separated from the shaft 38, the shaft 38, in the preferred embodiment illustrated, is formed from a plastic or similar material, which may be cut with a conventional scissors, scalpel, or similar surgical device (not shown), adjacent the second handle 18. Alternatively, the shaft 38 may be releasably secured to the second handle 18, for example by providing the shaft 38 with a threaded end (not shown) for location in a correspondingly threaded aperture (not shown) in the second handle 18. As a further alternative, the shaft 38 could be releasably engaged to the mesh 14, with some form of actuator (not shown) being provided adjacent the handles 16, 18, in order to allow the remote separation of the shaft 38 from the mesh 14, adjacent the mesh 14. With such an arrangement, the body 12, containing the shaft 38, could then be removed from the surgical cavity, thereby leaving the mesh 14 in place against the site of the hernia. In that event, the shaft 38 need not then be formed from a plastic, and could also be used repeatedly, with a replacement mesh 14 simply being secured thereto. The releasable mesh 14 could for example be provided with the shaft mounting area 39 being in the form of a central aperture (not shown) suitably dimensioned such that mesh 14 could simply be pressed onto the shaft 38. Consequently, during use of the device 10, once the shaft 38 had been drawn rearwardly, or the inner tube 28 extended forwardly, such as to effect expansion of the mesh 14, further rearward withdrawal of the shaft 38, or further forward extension of the inner tube 28, would pull the shaft 38 out of engagement with the mesh 14, thereby leaving the parietal face of the mesh 14 in place against the site of the hernia.

Returning to the embodiment illustrated in FIGS. 1-5, once the body 12 has been removed, the mesh 14 will be left in place against the site of the hernia, with the majority of the shaft 38 still connected thereto. The collar 42 is preferably dimensioned to provide a friction fit with the shaft 38, in order to ensure that the collar 42 maintains its position on the shaft 38, as in FIG. 3, when the body 12 has been removed. At this point the shaft 38 is then re-cut, as close as possible to the collar 42, and the remainder of the shaft 38 discarded. At this point, the surgical incision providing access to the site of the hernia could be closed, by any suitable means, thereby holding the mesh 14 in place against the site of the hernia. However it will be appreciated that the severed end of the shaft 40, adjacent the collar 42, would then be protruding into the soft tissue of the parietal wall, for example the abdominal wall, which may cause some discomfort. In order to avoid this, the device 10 preferably further comprises an abutment in the form of a disc 50 (shown in FIG. 4), which in practice will be approximately 20 to 50 mm in diameter, the disc 50 being provided with a recess 52 therein. Thus, before the surgical incision is closed, the disc 50 is positioned against the mesh 14, with the cut end of the shaft 38 seated within the recess 52, such that the disc 50 faces outwardly towards the abdominal wall. The surgical incision is then closed over the disc 50, which therefore serves to cover the cut end of the shaft 38, in addition to distributing the pressure exerted by same over a larger area, further decreasing any discomfort which may otherwise be experienced. It will be appreciated that the disc 50 may be of any suitable shape and configuration, once capable of performing the intended function of same.

Figure 6:
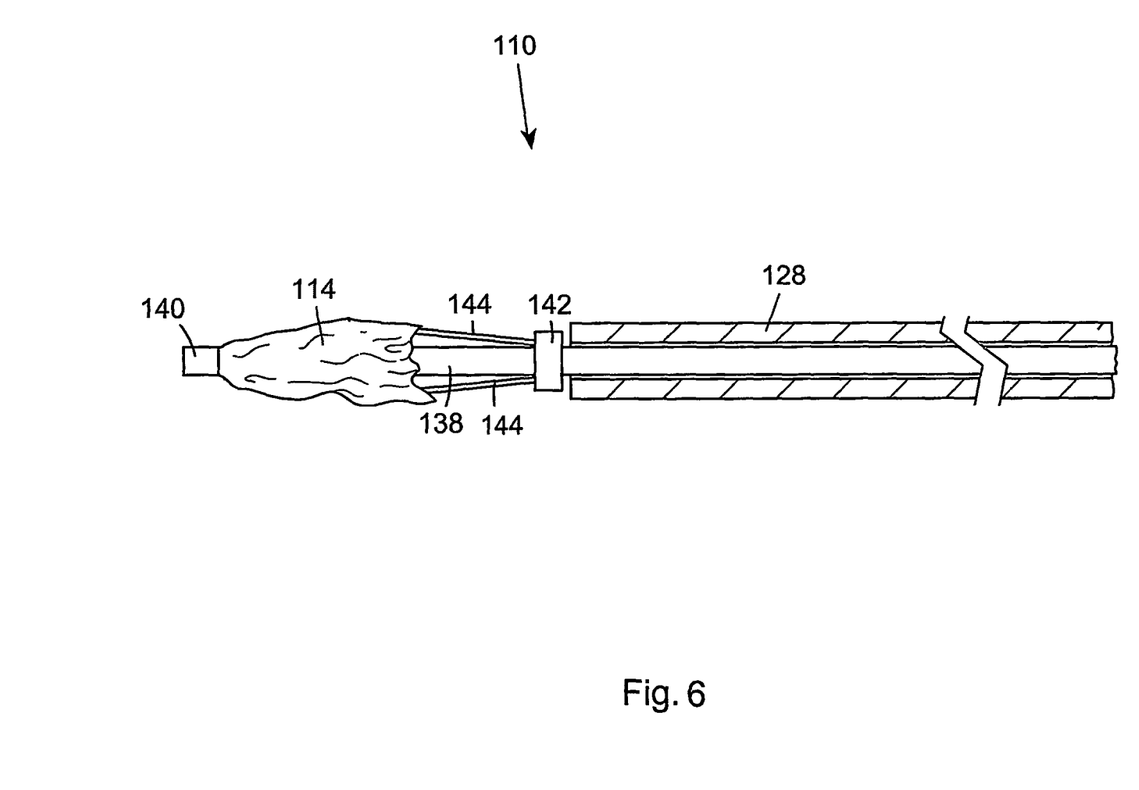
FIG. 6 illustrates a sectioned side elevation of an alternative, simplified embodiment of the device of FIG. 1, in an undeployed configuration.

Referring now to FIG. 6 of the drawings, there is illustrated an alternative embodiment of a surgical device according to the present invention, generally indicated as 110. In this alternative embodiment, like components have been accorded like reference numerals, and unless otherwise stated, perform a like function. From this alternative embodiment, it will be apparent that the method of surgical repair according to the present invention could be conducted using only a mesh 114 and shaft 138 arrangement, including a collar 142 and arms 144, and optionally an inner tube 128. Thus, following the creation of a suitable surgical incision, the mesh 114, collapsed about the shaft 138, could be passed through the surgical incision using the shaft 138, possibly housed within the inner tube 128 as illustrated, until the mesh 114 is located at the site of the hernia. At this point, the collar 142 would be displaced towards the mesh 114, using the inner tube 128 as hereinbefore described with reference to the device 10, in order to effect the expansion of the mesh 114. The inner tube 128 could however be omitted, with displacement of the collar 142 being achieved by drawing the shaft 138 back through the surgical incision, wherein the collar 142 would catch on, or be arrested by, the edges of the surgical incision, thus holding the collar 142 stationary, while the shaft 138, and therefore the mesh 114, are drawn rearwardly through and towards same respectively. In either event, the shaft 138 could then be severed from the mesh 114 as described above with reference to the device 10, or if a press fit is provided between the mesh 114 and shaft 138, simply pulled out of the mesh 114. Following removal of the shaft 138, the mesh 114 may be sutured or otherwise secured in place, and the surgical incision closed.

Both the mesh 14; 114, and the disc 50 are formed from both a biocompatible, and optionally biodegradable material, thereby avoiding the need for a second surgical procedure to remove same, the mesh 14; 114 and the disc 50 simply dissolving over time, although not before the site of the hernia has had sufficient time to adequately heal. The length of time necessary to dissolve the mesh 14; 114 and the disc 50 may be varied by altering the materials chosen, or the properties of the materials chosen. It is not however essential that the mesh 14; 114 and disc 50 are biodegradable.

It will also be appreciated that, were the shaft 38 releasably engagable adjacent the shaft mounting area 39 of the mesh 14, the use of the disc 50 would be less beneficial.

It will be apparent that any suitable materials may be chosen for the various components comprised in the device 10; 110. For example, in order to reduce the cost and simplify the manufacture of the device 10; 110, all of the parts could be formed from a plastic or combination of plastics. The device 10; 110 could therefore be supplied in a hermetically sealed container or pouch (not shown), the device 10; 110 having been suitably sterilised prior to being sealed in same. The device 10; 110 would thus likely be a single use item, to be suitably discarded following use, as it might be uneconomic to re-sterilise the device 10; 110.

It is preferable that all components except the mesh 14; 114 and the disc 50 are formed from a metal or ceramic, for example stainless steel or titanium, allowing the device 10; 110 to be cleaned and sterilised after each use, for example in a conventional autoclave (not shown). The suitability of such materials for use in the manufacture of surgical implements is well documented, and although the initial cost would be greater, the device 10; 110 could be used repeatedly.

The mesh 14; 114 could also be manufactured from a number of suitable materials, although it is of course highly preferable that the mesh 14; 114 be flexible, in order to be capable of following the contours of the parietal wall, and to be capable of deforming in response to movement of the patient, when the mesh 14; 114 is secured in place. The flexibility of the mesh 14; 114 also renders same suitable for collapsed storage about or within the device 10; 110. The mesh 14; 114 could for example be manufactured from polypropylene. Suitable materials for the mesh 14; 114 are manufactured by a number of companies, for example the Parietex® range manufactured by Sofradim International, France. Other suitable materials are produced by United States Surgical Corporation, of Connecticut, United States, or by Davol Inc. of Rhode Island, United states, to name but a few.

The device 10; 110 of the present invention thus provides a simple yet highly effective device and method for accurately locating and securing a parietal reinforcement implant against the site of a hernia, in order to aid in the healing of same.

The invention claimed is:

1. A device for use in parietal surgery, the device comprising:
   a body;
   a shaft movably disposed along the body;
   a parietal surgical implant in the form of a mesh adapted for use in repairing hernias, the parietal surgical implant being locatable in a collapsed state within the body, the parietal surgical implant being adapted to be displaceable between the collapsed state and an expanded state;
   a mechanism for expanding the parietal surgical implant from the collapsed state into the expanded state;
   a mechanism for retaining the parietal surgical implant within the body in the collapsed state, the retaining mechanism comprising a sleeve within which the parietal surgical implant is locatable, the sleeve being displaceable relative to the parietal surgical implant in order to expose the parietal surgical implant;
   the mesh of the parietal surgical implant having a mesh perimeter and a shaft mounting area, the mesh being mounted to the shaft via the shaft mounting area;
   the expanding mechanism comprising a collar slidably mounted about the shaft, and at least one arm mounted between the collar and an arm mounting position of the mesh, the arm mounting position being spaced apart from the shaft mounting area, the collar being displaceable towards the mesh in order to urge the mesh towards the expanded state; and
   an abutment seated against the collar and a cut end of the shaft to retain the mesh in its expanded state at the hernia once the cut end of the shaft is separated from a remainder of the shaft, the abutment having a recess within which the cut end of the shaft is seated, such that the abutment covers the cut end of the shaft and distributes pressure exerted by the cut end of the shaft following the closure of a surgical incision through which the hernia is accessed by the device.

2. A device according to claim 1 in which the body is provided with means for gripping the body in order to facilitate manipulation of the device.

3. A device according to claim 2 further comprising an actuator operable to effect displacement of the sleeve relative to the parietal surgical implant, the actuator being located at or adjacent the gripping means, the actuator being operatively associated with the sleeve.

4. A device according to claim 3 in which the actuator is mounted for slidable engagement with the body.

5. A device according to claim 1 in which the expanding mechanism comprises a plurality of arms mounted about the collar, the plurality of arms being secured to a plurality of the arm mounting positions of the mesh, the arm mounting positions being spaced apart from the shaft mounting area.

6. A device according to claim 5 in which the plurality of arm mounting positions are spaced apart on the mesh perimeter.

7. A device according to claim 5 in which the mesh is substantially circular and the shaft mounting area is located substantially centrally therein; and
the plurality of arm mounting positions are circumferentially spaced apart on the mesh perimeter.

8. A device according to claim 1 in which the arm mounting position is located adjacent the mesh perimeter.

9. A device according to claim 1 in which the shaft mounting area is substantially centrally located.

10. A device according to claim 1 in which the shaft is provided with a shaft handle displaceable relative to the body, such that the mesh may be drawn towards the expanding mechanism in order to effect expansion of the mesh.

11. A device according to claim 1 in which the mesh is separable from the shaft.

12. A device according to claim 1 in which the mesh and the shaft are adapted for a press fit engagement.

13. A device according to claim 1 in which the shaft is formed from a material which may be cut by conventional surgical equipment.

14. A device according to claim 1 in which the body is provided with a distensible member thereon.

15. A device according to claim 14 in which the distensible member comprises a balloon connectable to a fluid supply in order to effect the inflation thereof.

16. A device according to claim 1 in which the parietal surgical implant is formed from a biodegradable material.

17. A device according to claim 1, further comprising a parietal surgical implant for use as a replacement part for a device according to claim 1, the parietal surgical implant being provided in a collapsed state, and being adapted to be displaceable between the collapsed state and an expanded state.

18. A parietal surgical implant according to claim 17 in which the expanding mechanism comprises a plurality of arms mounted about the collar, the plurality of arms being secured to a plurality of the arm mounting positions of the mesh, the arm mounting positions being spaced apart from the shaft mounting area.

19. A device according to claim 1 further comprising an actuator operable to effect displacement of the sleeve relative to the parietal surgical implant.

20. A device according to claim 1 in which the body is of elongate tubular form.

21. A method of surgical repair at a surgical repair site, comprising the steps of:
providing a device according to claim 1;
passing the parietal surgical implant, in the collapsed state, through an incision into a position adjacent the surgical repair site;
expanding the parietal surgical implant from the collapsed state into an expanded state; and
securing the parietal surgical implant against the surgical site by locating the abutment against the mesh of the parietal surgical implant before closing the incision.

22. A device for use in parietal surgery, the device comprising:
a body;
a shaft movably disposed along the body;
a parietal surgical implant in the form of a mesh adapted for use in repairing hernias, the mesh having a mesh perimeter, a shaft mounting area that receives the shaft to mount the mesh to the shaft, and an arm mounting position that is spaced from the shaft mounting area, the mesh being locatable in a collapsed state within the body, and the mesh being displaceable between the collapsed state and an expanded state;
a collar slidably mounted about the shaft, the collar and the mesh being displaceable relative to one another in order to expand the mesh from the collapsed state into the expanded state;
at least one arm mounted between the collar and the arm mounting position of the mesh, the at least one arm being operable to expand the mesh toward the expanded state when the collar and the mesh are displaced relative to one another;
a sleeve for retaining the mesh within the body in the collapsed state, the mesh being locatable within the sleeve, and the sleeve being displaceable relative to the mesh in order to expose the mesh; and
an abutment configured to be seated against the collar and a cut end of the shaft to retain the mesh in its expanded state at the hernia once the cut end of the shaft is separated from a remainder of the shaft, the abutment having a recess within which the cut end of the shaft is seated, such that the abutment covers the cut end of the shaft and distributes pressure exerted by the cut end of the shaft following the closure of a surgical incision through which the hernia is accessed by the device.

* * * * *